United States Patent [19]

Herber et al.

[11] 4,076,642
[45] Feb. 28, 1978

[54] NOVEL MONOEPOXY COMPOUNDS AS ACID SCAVENGERS IN FUNCTIONAL FLUIDS

[75] Inventors: John F. Herber, St. Louis; William R. Richard, Jr.; Robert W. Street, both of Kirkwood, all of Mo.

[73] Assignee: Monsanto Company, St. Louis, Mo.

[21] Appl. No.: 685,222

[22] Filed: May 11, 1976

Related U.S. Application Data

[63] Continuation-in-part of Ser. No. 454,539, Mar. 25, 1974, abandoned.

[51] Int. Cl.$^2$ .................. C10M 3/40; C10M 3/20; C10M 3/14; C07D 303/12
[52] U.S. Cl. .................. 252/78.5; 252/49.8; 252/49.9; 252/57; 252/79; 252/389 A; 252/396; 260/348.54
[58] Field of Search ........... 260/348 C; 252/79, 78.5, 252/389 A, 396, 49.8, 49.9, 57

[56] References Cited

U.S. PATENT DOCUMENTS

| 3,187,018 | 6/1965 | Tinsley et al. | 260/348 C |
| 3,723,320 | 3/1973 | Herber et al. | 252/78 |
| 3,941,709 | 3/1976 | Herber et al. | 252/78 |

FOREIGN PATENT DOCUMENTS

| 752,874 | 2/1967 | Canada | 260/348 C |

OTHER PUBLICATIONS

Crundwell et al., J. Chem. Soc., (1964), pp. 1400–1405.
Liotta et al., J. Chem. Soc., D (1971) (20), pp. 1312–1313.
Medved et al., J. Chem. Eng. Data 9(2) (1964), p. 240.
Zalkow et al., Jour. Org. Chem., vol. 34, No. 1, Jan. 1969, pp. 218–220.

*Primary Examiner*—Harris A. Pitlick
*Attorney, Agent, or Firm*—William H. Duffey

[57] ABSTRACT

A new class of monoepoxyethylenecyclohexyl compounds useful as acid scavengers and corrosion inhibitors in functional fluid compositions.

18 Claims, No Drawings

NOVEL MONOEPOXY COMPOUNDS AS ACID SCAVENGERS IN FUNCTIONAL FLUIDS

FIELD OF THE INVENTION

This application is a continuation-in-part of copending application Ser. No. 454,539, filed Mar. 25, 1974 now abandoned.

This invention relates to a new class of monoepoxyethylenecyclohexyl compounds and to functional fluid compositions, particularly hydraulic fluids, containing such compounds to inhibit acid buildup.

BACKGROUND OF THE INVENTION
DESCRIPTION OF THE PRIOR ART

Functional fluids have been utilized in many different types of applications such as electronic coolants, diffusion pump fluids, lubricants, damping fluids, bases for greases, power transmission and hydraulic fluids, heat transfer fluids, heat pump fluids, refrigeration equipment fluids and as filter mediums for air-conditioning systems. Of these uses, hydraulic fluids intended for use in the hydraulic system of aircraft for operating various mechanisms and aircraft control systems must meet stringent functional and use requirements. One of the most important requirements for an aircraft hydraulic fluid is that the fluid be chemically stable to resist oxidative and thermal degradation which can result in the formation of acid and the corrosive attack of metals in contact with the hydraulic fluid.

In order to control the degree of acid buildup during use of the fluid and inhibit corrosion of the components in the hydraulic system, it is conventional to add certain acid scavengers and/or corrosion inhibitors to the hydraulic fluid base stock.

Although a variety of compounds have been suggested for use as corrosion inhibitors, acid acceptors which act as proton acceptors and prevent the buildup of corrosive acids in the fluids when they undergo decomposition under prolonged use at high temperatures are generally preferred. A particularly preferred class of such materials comprises epoxy compounds, especially epoxidized naturally occurring materials such as epoxidized unsaturated glycerides including epoxidized soybean oil, epoxidized castor oil, epoxidized linseed oil, epoxidized fats and the like. Other suggested materials include epoxy esters such as butylepoxyacetoxystearate, glyceryl triepoxyacetoxystearate, isooctylepoxystearate, epoxidized isooctyl phthalate and the like. Also suggested are various alkyl and arylalkyl epoxides such as epoxy decane, epoxy hexadecane, epoxy octadecane, epoxy cyclododecane, and the like, and glyceryl and various glycidyl ethers such as phenyl glycidyl ether, glycidyl cyclohexyl ether, alkyl glycidyl ether, and the like.

More recently it has been suggested that a particular class of epoxy compounds, 3,4-epoxycycloalkyl-3,4-epoxycycloalkyl carboxylates, are particularly useful as acid acceptors for hydraulic fluids and are more effective than the epoxy compounds used heretofore. A particularly preferred compound is 3,4-epoxycyclohexylmethyl-3,4-epoxycyclohexane carboxylate. These compounds are well known chemical entities which have been used as acid scavengers for chlorinated diphenyl dielectric fluids prior to their introduction as inhibitors for hydraulic fluids.

Although 3,4-epoxycycloalkyl-3,4-epoxycycloalkyl carboxylates are effective acid scavengers for common hydraulic fluid compositions, they have a disadvantage in that they cause resinous deposits to form around the fluid pump shaft at the point of seal. The formation of deposits is of particular concern in aircraft hydraulic systems which operate under pressure and where the deposits soon result in fluid leakage through the seal. Although the problem of shaft seal leakage is not serious from an aircraft operational point of view, it represents a sufficient nuisance that the aircraft industry and aircraft hydraulic fluid manufacturers have actively sought alternative acid acceptors which are as effective and efficient as the 3,4-epoxycyclohexylmethyl-3,4-epoxycyclohexane carboxylate but which do not have the deposit and leakage problem associated with this material.

It is accordingly an object of this invention to provide an acid acceptor effective to prevent acid buildup in functional fluid compositions. Another object of this invention is to provide an acid acceptor which can be used without adverse secondary effects in functional fluids which may also contain a polymeric V.I. improver. A further object of this invention is to provide functional fluid compositions which are resistant to thermal and oxidative degradation and which are suitable for use in aircraft hydraulic systems. It is a yet further object of this invention to provide an aircraft hydraulic fluid containing a polymeric V.I. improver and an epoxide acid acceptor which does not cause pump shaft seal leakage. Still another object of this invention is to provide a method for operating a hydraulic pressure device utilizing a functional fluid containing an epoxide acid acceptor and a polymeric V.I. improver. Yet further objects will be apparent from the following description of the invention.

SUMMARY

In accordance with this invention, it was surprisingly found that novel compounds which effectively prevent acid build-up in functional fluid compositions are represented by the following formula:

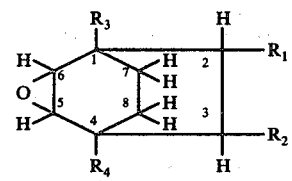

FORMULA I wherein $R_1$ is —$(CH_2)_{0-3}$—C(O)R or —$CH_2OR$; R is an alkyl radical having from 1 to about 18 carbon atoms; $R_2$ is $R_1$, hydrogen or an alkyl radical having from 1 to about 9 carbon atoms; $R_3$ and $R_4$ are individually hydrogen or an alkyl radical having from 1 to about 4 carbon atoms. Preferably, R is an alkyl radical having from 3 to about 15 carbon atoms, even more preferably R is an alkyl radical having from 5 to 10 carbon atoms.

DESCRIPTION OF THE PREFERRED EMBODIMENTS

Preferred epoxy compounds that may be employed in the practice of this invention are those represented by Formula I wherein $R_1$ is —$(CH_2)_{0-3}$—C(O)OR, —C(O)R or $CH_2OR$; R is an alkyl radical having from 3 to about 15 carbon atoms; $R_2$ is hydrogen, an alkyl radical having from 1 to about 9 carbon atoms, —$(CH_2)_{0-3}$—C-

(O)OR', —C(O)R' or CH₂OR'; R' is an alkyl radical having from 1 to about 18 carbons; R₃ and R₄ are individually hydrogen or an alkyl radical having from 1 to 4 carbon atoms. Preferably R is an alkyl radical having from 5 to about 10 carbon atoms.

Typical novel compounds of this invention include, but are not limited to, the following:

DIESTERS

Diethyl 5,6-epoxy-1,4-ethylenecyclohexane-2,3-dicarboxylate,
Dihexyl 5,6-epoxy-1,4-ethylenecyclohexane-2,3-dicarboxylate,
Diheptadecyl 5,6-epoxy-1,4-ethylenecyclohexane-2,3-dicarboxylate,
Butyl methyl 5,6-epoxy-1,4-ethylenecyclohexane-2,3-dicarboxylate,
Didecyl 5,6-epoxy-1-ethyl-1,4-ethylenecyclohexane-2,3-dicarboxylate,
Didodecyl 5,6-epoxy-1-methyl-4-butyl-1,4-ethylenecyclohexane-2,3-dicarboxylate,
Ditetradecyl-5,6-epoxy-1,4-ethylenecyclohexane-2,3-di-(methylenecarboxylate),
Di(2-ethylhexyl)-5,6-epoxy-1,4-ethylenecyclohexane-2,3-di-(ethylenecarboxylate).

ETHERS

2-Methoxy-5,6-epoxy-1,4-ethylenecyclohexane,
2-Hexoxy-5,6-epoxy-1,4-ethylenecyclohexane,
2-Decoxy-5,6-epoxy-1,4-ethylenecyclohexane,
2-Octadecoxy-5,6-epoxy-1,4-ethylenecyclohexane,
2-Ethoxy-5,6-epoxy-1-methyl-1,4-ethylenecyclohexane,
2-Nonoxy-5,6-epoxy-4-ethyl-1,4-ethylenecyclohexane.

DIETHERS 2,3-Diethoxy-5,6-epoxy-1,4-ethylenecyclohexane,
2,3-Diheptoxy-5,6-epoxy-1,4-ethylenecyclohexane,
2,3-Didodecoxy-5,6-epoxy-1,4-ethylenecyclohexane,
2,3-Dipentoxy-5,6-epoxy-4-butyl-1,4-ethylenecyclohexane,
2,3-Dioctoxy-5,6-epoxy-1-methyl-4-butyl-1,4-ethylenecyclohexane.

KETONES

Propyl 5,6-epoxy-1,4-ethylenecyclohexylketone,
2-Ethylhexyl-5,6-epoxy-1,4-ethylenecyclohexyl ketone,
Pentadecyl-5,6-epoxy-1,4-ethylenecyclohexyl ketone,
Octadecyl-5,6-epoxy-1-propyl-1,4-ethylenecyclohexyl ketone,
Nonyl-5,6-epoxy-4-butyl-1,4-ethylenecyclohexyl ketone.

DIKETONES

Dibutyl-5,6-epoxy-1,4-ethylenecyclohexyl diketone,
Dihexadecyl-5,6-epoxy-1,4-ethylenecyclohexyl diketone,
Diethyl-5,6-epoxy-1,4-ethylenecyclohexyl diketone,
Didodecyl-5,6-epoxy-1-methyl-1,4-ethylenecyclohexyl diketone.

Particularly preferred epoxy compounds that can be employed in the practice of this invention are those represented by the following formula:

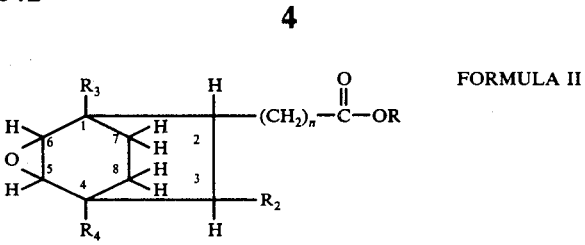

FORMULA II wherein R₂ is hydrogen or an alkyl radical having from 1 to about 9 carbon atoms; R₃ and R₄ are individually hydrogen or an alkyl radical having from 1 to about 4 carbon atoms; R is an alkyl radical having from 1 to about 18 carbon atoms and $n$ is an integer of from 0 to 3. Preferably, R is an alkyl radical having from 3 to about 15 carbon atoms, even more preferably R is an alkyl radical having from 5 to 10 carbon atoms; R₂, R₃ and R₄ are hydrogen and $n$ is 0. Representative examples of these compounds include, but are not limited to, methyl 5,6-epoxy-1,4-ethylenecyclohexane-2-carboxylate, decyl 5,6-epoxy-1,4-ethylenecyclohexane-2-carboxylate, heptadecyl 5,6-epoxy-1,4-ethylenecyclohexane-2-carboxylate, ethyl 5,6-epoxy-1-ethyl-1,4-ethylenecyclohexane-2-methylenecarboxylate, 2-ethylhexyl 5,6-epoxy-1,4-ethylenecyclohexane-2-carboxylate, methyl 5,6-epoxy-1,4-ethylenecyclohexane-2-ethylene carboxylate.

These compounds may be prepared by those procedures well known in the art, such as, for example, those procedures described in U.S. Pat. No. 3,187,018.

The epoxy esters of this invention may be prepared by first reacting cyclohexadiene with an alkyl acrylate. The reaction product is converted to the epoxy esters of this invention by oxidizing the olefinic linkage contained in the reaction product. Peracetic acid is particularly well suited for this reaction, since it may be carried out under relatively mild conditions and with a minimum of operating difficulty.

The diesters of this invention may be prepared by first reacting cyclohexadiene with maleic anhydride and then reacting this reaction product with an appropriate alcohol. Epoxidation is achieved by oxidizing the olefinic linkage with peracetic acid.

Epoxy mono ethers of this invention are prepared in the same manner as epoxy mono esters except an alkyl acrylyl ether is used in place of the alkyl acrylate. Diethers are prepared by using a compound having the formula R—O—CH₂—CH=CH—CH₂-O-R.

Epoxy mono ketones of this invention are prepared by using alkyl vinyl ketones in place of the alkyl acrylate used to prepare the epoxy mono esters. Epoxy diketones are prepared by using a compound having the formula R—C(O)—CH=CH—C(O)—R.

Functional fluid compositions of this invention comprise a major amount of at least about 50 percent by weight of a base stock material selected from the group consisting of esters or amides of an acid of phosphorus, di- or tricarboxylic acid esters, esters of polyhydric compounds and mixtures thereof, from 0 to minor amounts of one or more other base stock materials or base stock modifiers, and from about 0.1 to 15 percent by weight of one of the epoxy compounds of this invention. The compositions may include polymeric V.I. improvers and other conventional additives and are particularly useful as aircraft hydraulic fluids.

The concentration of the epoxy compound in the functional fluid is adjusted according to the demands of the system and nature of the base stock being employed in order to provide compositions which contain sufficient amounts of epoxy material to inhibit acid buildup during normal operation. It has been found that the concentration of epoxy compound required to inhibit and control acid buildup in a particular base stock varies according to the composition of the base stock or blends of base stocks. It has generally been found that preferred additive levels of epoxy compounds are from 0.10 weight percent to 10.0 weight percent, although concentrations of 15 percent or higher are also effective and may be used. Thus, included in the present invention are functional fluid compositions comprising a base stock material and any of the epoxy compounds represented by Formula I in a concentration sufficient to control and inhibit acid buildup in the base stock. The fluid compositions of this invention can be compounded in any manner known to those skilled in the art for incorporating an additive into a base stock, as for example by adding the epoxy compound to the base stock with stirring until a uniform fluid composition is obtained.

As mentioned, the base stock material which comprises at least about 50% by weight of the functional fluids of the present invention, is selected from the group consisting of esters and amides of an acid of phosphorus, di- or tricarboxylic acid esters, esters of polyhydro compounds, and mixtures thereof. These base stock materials and examples thereof are described in U.S. Pat. No. 3,723,320.

Hydrocarbon phosphates are preferred. Phosphorus ester base stocks include trialkyl phosphates, triaryl and/or alkyl substituted aryl phosphates and mixed aryl and/or substituted arylalkyl phosphates. With respect to the alkyl groups, it is preferred to have from about 2 to about 18 carbon atoms, more preferably from about 2 to about 12 carbon atoms and with respect to the aryl and substituted aryl groups, it is preferred to have from about 6 to about 16 carbon atoms and more preferably from about 6 to about 12 carbon atoms. Typical examples of preferred phosphates are dibutylphenyl phosphate, triphenyl phosphate, tricresyl phosphate, tributyl phosphate, tri-2-ethylhexyl phosphate, trioctyl phosphate, the phosphates described in U.S. Pat. No. 3,723,315, such as di(nonylphenyl) phenyl phosphate, di(cumylphenyl) phenyl phosphate, (cumylphenyl) (nonylphenyl) phenyl phosphate, and mixtures of the above phosphates such as mixtures of tributyl phosphate and tricresyl phosphate, mixtures of triphenyl phosphate and 2-ethylhexyl diphenyl phosphate, mixtures of cumylphenyl diphenyl phosphate, nonylphenyl diphenyl phosphate, 2-ethylhexyl diphenyl phosphate and triphenyl phosphate. A preferred mixture contains 45 to 65% triphenyl phosphate, 25 to 45% by weight of the reaction product of 1.5 to 2 moles of nonylphenol, 0.5 to 1 mole of cumylphenol, 6 to 7 moles of phenol with 3 moles of phosphorus oxychloride and 5 to 15% of 2-ethylhexyl diphenyl phosphate. All percentages are by weight based on the total weight of the mixture.

In addition to these base stock materials, the functional fluid may contain up to about 50 percent of one or more other base stock materials. Examples of these other base stock materials are given in U.S. Pat. No. 3,723,320. Although it is not permissible to employ these other base stock materials in major amounts in fluid compositions of the instant invention, they may be used singly or in combinations as a minor component of the total base stock present in amounts of less than about 50 percent by weight.

In addition to the base stock materials and a monoepoxy compound defined by Formula I, the fluids of the instant invention may also contain one or more base stock modifiers. As used herein, "base stock modifier" means any material which when added to the base stock effects a determinable change in the chemical or physical properties of the base stock. Examples of typical classes of such modifiers which are widely used in formulating hydraulic and other functional fluids include dyes, pour point depressants, antioxidants, antifoam agents, viscosity index improvers such as polyalkyl acrylates, polyalkyl methacrylates, polycyclic polymers, polyurethanes, polyalkylene oxides and polyesters, lubricity agents and water.

The preferred polymeric viscosity index improvers which may be employed in the compositions of this invention are the polymers of alkyl esters of unsaturated monocarboxylic acids having the formula

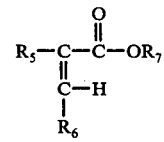

wherein $R_5$ and $R_6$ are each individually hydrogen or a $C_1$ to about $C_{10}$ alkyl group, and $R_7$ is a $C_1$ to about $C_{12}$ alkyl group. Illustration of the alkyl groups represented by $R_5$, $R_6$ and $R_7$ within their definitions as given above are for example methyl, ethyl, propyl, butyl, t-butyl, isopropyl, 2-ethylhexyl, hexyl, decyl, undecyl, dodecyl and the like. These polymers include, for example, poly(butylmethacrylates), poly(hexylmethacrylates), poly(octylacrylates), poly(dodecylacrylates) and polymers wherein the ester is a mixture of compounds obtained by esterifying the $\alpha$-$\beta$ unsaturated monocarboxylic acid with a mixture of mono-alcohols containing from 1 to 12 carbon atoms. These and other "base stock modifiers" are described in U.S. Pat. No. 3,723,320.

In a preferred embodiment of the present invention the functional fluid compositions comprise at least about 50 percent by weight of a phosphate ester or mixture of phosphate esters represented by the structure

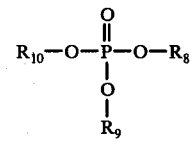

wherein $R_8$, $R_9$, and $R_{10}$ are hydrocarbon radicals selected from the group consisting of alkyl, alkoxyalkyl, aralkyl, aroxyalkyl, aryl, aroxyaryl, alkoxyaryl, alkaryl, and mixtures thereof and halogenated and alkyl-substituted members thereof having up to about 18 carbon atoms, and from about 0.1 to 15 percent by weight of an epoxy compound as hereinbefore defined. In addition to the phosphate ester and epoxy compound, these preferred fluid compositions can also contain certain additives as hereinbefore defined and can also contain minor amounts, e.g., less than about 50 percent by weight of one or more other base stock compositions as hereinbefore defined.

Particularly preferred functional fluid compositions comprise at least about 65 percent by weight of such phosphate esters and less than about 35 percent by weight of other materials including base stocks and base stock modifiers, and even more preferably contain at least about 80 percent by weight of such phosphate esters and less than about 20 percent by weight of other materials. Particularly preferred phosphate esters for use in the compositions of this invention are dialkylaryl phosphates wherein the alkyl radicals have 1 to 18 carbon atoms, e.g., dibutylphenyl phosphate, and mixtures of trialkyl phosphate and triaryl phosphate such as 88/12 tributyl phosphate/tricresyl phosphate.

The invention will now be illustrated by the following Examples. All parts and percentages are by weight unless otherwise stated.

EXAMPLE I

To a suitable reaction vessel was charged 267 gm of 2-ethylhexyl acrylate and then 4.1 gm of aluminum trichloride. Next 99.6 gm of 1,3 cyclohexadiene was added over about 1.5 hour period. The temperature ranged from 87° to 95° C.

The reaction mixture was washed in 1 M HCl and the organic and aqueous layers separated. The organic layer was distilled yielding 9.1 gm of the 2-ethylhexyl ester of cyclohexadiene.

To a suitable vessel was charged 69.2 gm of this ester. 56.05 gm of metachloroperbenzoic acid dissolved in 450 ml methylene chloride was slowly added over a 1 hour period. The temperature of the reaction mixture was maintained at 18° to 20° C. by using an ice bath. After the addition of the acid 300 ml of water containing 25 gm of $NaHCO_3$ and 4.5 gm $Na_2S_2O_5$ was added.

The reaction mixture was allowed to stand overnight. It was then washed and the organic layer separated. The solvent was removed by distillation. The reaction yielded 73.2 gm of 2-ethylhexyl-5,6-epoxy-1,4-ethylenecyclohexane-2-carboxylate.

Test results of a fluid containing this epoxide are given in the Table below.

TABLE

| Test No. | Base Fluid | Percent Epoxide | Acid[1] Buildup | Corrosion Rate, $mg/cm^2$ | | | | | |
|---|---|---|---|---|---|---|---|---|---|
| | | | | Mg | Al | Cd | Fe | Cr | Ag |
| 1 | * | 6.89 | >150 | −1.18 | −0.04 | −0.26 | −0.04 | −0.47 | −0.07 |

*Base Fluid comprises 87% dibutyl phenyl phosphate, 5.1% polyalkylmethacrylate polymer V.I. improver; 0.2% water.
[1]Acid buildup, hours to 0.50 titratable acid number (TAN)

In the preceding test, the stability of the fluid to oxidative and acid buildup was determined by maintaining the fluid at 275° F. and periodically titrating samples of the fluid to monitor the acid buildup. A titratable acid number (TAN) of 0.50 was taken as the end point, and the number of hours required for the fluid to reach this level of acid content was recorded as the acid buildup figure. Corrosion rates were determined and given as metal loss in $mg/cm^2$.

While this invention has been described with respect to various specific examples and embodiments, it is to be understood that the invention is not limited thereto and that it can be variously practiced within the scope of the following claims.

The embodiments of this invention in which an exclusive property or privilege is claimed are defined as follows:

1. A compound represented by the formula

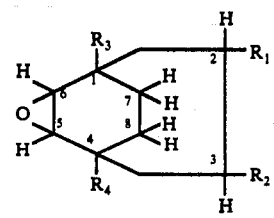

wherein $R_1$ is $-(CH_2)_{0-3}-C(O)OR$, $-CH_2OR$; R is an alkyl radical having from 3 to about 15 carbon atoms; $R_2$ is $R_1$, hydrogen or an alkyl radical having from 1 to about 9 carbon atoms; $R_3$ and $R_4$ are individually hydrogen or an alkyl radical having from 1 to about 4 carbon atoms.

2. A compound as defined in claim 1 wherein R is an alkyl radical having from 5 to about 10 carbon atoms.

3. A compound as defined in claim 1 wherein $R_2$ is $R_1$ or an alkyl radical having from 1 to about 9 carbon atoms.

4. A compound represented by the formula

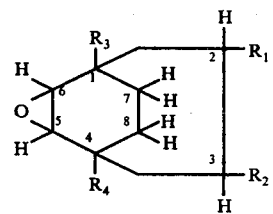

wherein $R_1$ is $-(CH_2)_{0-3}-C(O)R$, $-C(O)R$ or $CH_2OR$; R is an alkyl radical having from 3 to 15 carbon atoms; $R_2$ is hydrogen, an alkyl radical having from 1 to about 9 carbon atoms, $-(CH_2)_{0-3}-C(O)OR'$, $-C(O)R'$ or $CH_2OR'$; R' is an alkyl radical having from 1 to about 18 carbon atoms; $R_3$ and $R_4$ are individually hydrogen or an alkyl radical having from 1 to about 4 carbon atoms.

5. A compound as defined in claim 4 wherein R is an alkyl radical having from 5 to about 10 carbon atoms.

6. A hydraulic fluid composition comprising
(A) at least about 50 percent by weight of a base stock material selected from the group consisting of esters and amides of an acid of phosphorus, di- or tricarboxylic acid esters, esters of polyhydric compounds, and mixtures thereof, and
(B) from about 0.1 to 15 percent by weight of an epoxide compound represented by the structure

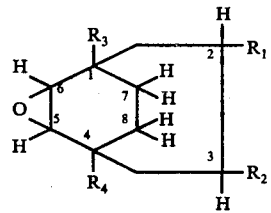

wherein $R_1$ is $-(CH_2)_{0-3}-C(O)OR$, $-C(O)R$ or $CH_2OR$; R is an alkyl radical having from 3 to about 15 carbon atoms; $R_2$ is hydrogen, an alkyl radical having from 1 to about 9 carbon atoms, $-(CH_2)_{0-3}-C(O)OR'$, $-C(O)R'$ or $CH_2OR'$; $R'$ is an alkyl radical having from 1 to about 18 carbon atoms; $R_3$ and $R_4$ are individually hydrogen or an alkyl radical having from 1 to about 4 carbon atoms.

7. A hydraulic fluid composition comprising
(A) at least about 50 percent by weight of a base stock material selected from the group consisting of esters and amides of an acid of phosphorus, di- or tricarboxylic acid esters, esters of polyhydric compounds, and mixtures thereof, and
(B) from about 0.1 to 15 percent by weight of an epoxide compound represented by the structure

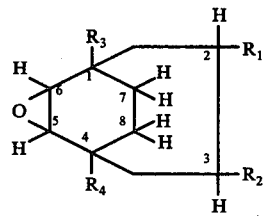

wherein $R_1$ is $-(CH_2)_{0-3}-C(O)OR$, $-C(O)R$, or $-CH_2OR$ where R is an alkyl radical having from 1 to about 18 carbon atoms, $R_2$ is $R_1$, hydrogen or an alkyl radical having from 1 to about 9 carbon atoms; $R_3$ and $R_4$ are individually hydrogen or an alkyl radical having from 1 to about 4 carbon atoms.

8. A composition of claim 7 wherein $R_1$ is $-(CH_2)_{0-3}-C(O)OR$.

9. A composition of claim 8 wherein the base stock material is a phosphate ester represented by the structure

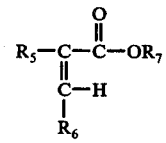

wherein $R_8$, $R_9$, and $R_{10}$ are hydrocarbon radicals selected from the group consisting of alkyl, alkoxyalkyl, aralkyl, aroxyalkyl, aryl, aroxyaryl, alkoxyaryl, alkaryl, and mixtures thereof and halogenated and alkyl-substituted members thereof having up to about 18 carbon atoms.

10. A composition of claim 9 wherein $R_{10}$ and $R_9$ are $C_{1-18}$ alkyl radicals and $R_8$ is a $C_{6-18}$ aryl radical.

11. A composition of claim 9 wherein the phosphate ester is a mixture of tributyl phosphate and triaryl phosphate.

12. A composition of claim 9 wherein the phosphate ester is dibutylphenylphosphate.

13. A composition of claim 12 wherein the epoxide compound is $C_{1-12}$ alkyl-5,6-epoxy-1,4-ethylenecyclohexane-2-carboxylate.

14. A composition of claim 13 wherein the epoxide compound is 2-ethylhexyl-5,6-epoxy-1,4-ethylenecyclohexane-2-carboxylate.

15. A functional fluid composition comprising a composition of claim 9 and from about 2 to 20 percent by weight of a viscosity index improver which is a polymer of an ester having the structure

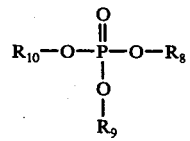

wherein $R_5$ and $R_6$ are each individually hydrogen or a $C_1$ to about $C_{10}$ alkyl group, and $R_7$ is a $C_1$ to about $C_{12}$ alkyl group.

16. A functional fluid composition comprising a composition of claim 9 and from about 2 to 20 percent by weight of a viscosity index improver which is a polymer of an alkylene oxide having a polymeric molecular weight of from about 1,500 to 4,500.

17. In a method of operating a hydraulic pressure device wherein a displacing force is transmitted to a displaceable member by means of a hydraulic fluid, the improvement which comprises employing as said fluid a composition of claim 7.

18. In a method of operating a hydraulic pressure device wherein a displacing force is transmitted to a displaceable member by means of a hydraulic fluid, the improvement which comprises employing as said fluid a composition of claim 15.

* * * * *

UNITED STATES PATENT AND TRADEMARK OFFICE
CERTIFICATE OF CORRECTION

PATENT NO. : 4,076,642
DATED : Feb. 28, 1978
INVENTOR(S) : John F. Herber et al.

It is certified that error appears in the above-identified patent and that said Letters Patent are hereby corrected as shown below:

Col. 1, line 57, after "compounds," there should be inserted -- the --

Col. 2, line 51, change "$-(CH_2)_{0-3}-C(O)R$" to read -- $(CH_2)_{0-3}-C(O)OR, -C(O)R$ --

Col. 8, line 11 (Claim 1), after the first formula there should be inserted: $-C(O)R$ or Col. 8, line 33 (Claim 4), change first $-C(O)R$ to $-C(O)OR$ Signed and Sealed this Eleventh Day of July 1978

[SEAL]

Attest:

RUTH C. MASON
*Attesting Officer*

DONALD W. BANNER
*Commissioner of Patents and Trademarks*

Disclaimer 4,076,642.—*John F. Herber*, St. Louis, *William R. Richard, Jr.* and *Robert W. Street*, Kirkwood, Mo. NOVEL MONOEPOXY COMPOUNDS AS ACID SCAVENGERS IN FUNCTIONAL FLUIDS. Patent dated Feb. 28, 1978. Disclaimer filed July 16, 1982, by the assignee, *Monsanto Co.*

Hereby enters this disclaimer of claims 1, 2, 3, 4, and 5 of said patent.
[*Official Gazette September 7, 1982.*]